(12) United States Patent
Knickerbocker et al.

(10) Patent No.: US 11,094,407 B2
(45) Date of Patent: Aug. 17, 2021

(54) ELECTRONICS MINIATURIZATION PLATFORM FOR MEDICATION VERIFICATION AND TRACKING

(71) Applicant: International Business Machines Corporation, Armonk, NY (US)

(72) Inventors: John Knickerbocker, Yorktown Heights, NY (US); Li-Wen Hung, Mahopac, NY (US); Bing Dang, Chappaqua, NY (US); Katsuyuki Sakuma, Fishkill, NY (US); Jeffrey Donald Gelorme, Burlington, CT (US); Rajeev Narayanan, Briarcliff Manor, NY (US); Qianwen Chen, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/440,032

(22) Filed: Jun. 13, 2019

(65) Prior Publication Data

US 2020/0395115 A1     Dec. 17, 2020

(51) Int. Cl.
*G16H 20/10*     (2018.01)
*A61B 5/00*      (2006.01)
(Continued)

(52) U.S. Cl.
CPC ........... *G16H 20/10* (2018.01); *A61B 5/0031* (2013.01); *A61B 5/4839* (2013.01);
(Continued)

(58) Field of Classification Search
CPC ........ G16H 20/10; G16H 10/60; G16H 70/40; A61B 5/0031; A61B 5/4839;
(Continued)

(56) References Cited

U.S. PATENT DOCUMENTS 5,700,998 A * 12/1997 Palti ................. A61J 3/007
                                                    235/375
6,799,725 B1 * 10/2004 Hess ................. A61J 3/007
                                                    235/462.01

(Continued)

FOREIGN PATENT DOCUMENTS

WO     2009146082 A2    12/2009

OTHER PUBLICATIONS

C. Crema, A. Depari, A. Flammini, M. Lavarini, E. Sisinni, A. Vezzoli "A Smartphone-Enhanced Pill Dispenser Providing Patient Identification and In-Take Recognition" University of Brescia, Department of Information Engineering. 2015 [retrieved Aug. 27, 2018].

(Continued)

*Primary Examiner* — Adnan Aziz
(74) *Attorney, Agent, or Firm* — Harrington & Smith

(57) ABSTRACT

A drug delivery form includes a drug and electronics. The electronics includes memory(ies) having drug delivery form information, including information about the drug and about at least part of a supply chain from manufacture of the drug delivery form to a current location in the supply chain. The electronics includes communication circuitry configured to read data from and write data to the drug delivery form information. An apparatus includes memory(ies) having computer readable code, and processor(s). The processor(s) cause the apparatus to perform operations including communicating with a drug delivery form including a drug and drug delivery form information, including information about the drug and about at least part of a supply chain from manufacture of the drug delivery form to a current location in the supply chain. The processor(s) cause the apparatus to perform reading data from or writing data into the drug and drug delivery form information.

19 Claims, 7 Drawing Sheets

(51) Int. Cl.
*A61J 3/00* (2006.01)
*G16H 10/60* (2018.01)
*G16H 70/40* (2018.01)
*A61B 90/90* (2016.01)
*A61B 5/07* (2006.01)

(52) U.S. Cl.
CPC ............. *A61B 5/6831* (2013.01); *A61J 3/007* (2013.01); *G16H 10/60* (2018.01); *A61B 5/076* (2013.01); *A61B 5/4833* (2013.01); *A61B 5/681* (2013.01); *A61B 90/90* (2016.02); *A61J 2200/30* (2013.01); *G16H 70/40* (2018.01)

(58) Field of Classification Search
CPC ....... A61B 5/6831; A61B 5/076; A61B 5/681; A61B 5/4833; A61J 3/007; A61J 2200/30
See application file for complete search history.

(56) References Cited

U.S. PATENT DOCUMENTS

| | | | | |
|---|---|---|---|---|
| 6,800,060 | B2* | 10/2004 | Marshall | A61B 1/04 600/309 |
| 7,118,531 | B2* | 10/2006 | Krill | A61B 1/041 600/309 |
| 7,253,716 | B2* | 8/2007 | Lovoi | A61J 3/007 340/10.1 |
| 7,414,534 | B1* | 8/2008 | Kroll | A61B 5/0031 340/573.1 |
| 7,504,954 | B2* | 3/2009 | Spaeder | G06Q 50/24 340/573.1 |
| 8,269,635 | B2 | 9/2012 | Kroll et al. | |
| 8,518,022 | B2* | 8/2013 | Trovato | A61B 5/411 604/890.1 |
| 8,543,411 | B2* | 9/2013 | Koster | G06F 19/3462 705/2 |
| 8,564,432 | B2* | 10/2013 | Covannon | A61J 3/007 340/539.12 |
| 8,929,553 | B2* | 1/2015 | Bauchot | H04L 9/3234 380/278 |
| 9,576,264 | B2* | 2/2017 | Bolene | G16H 40/20 |
| 9,589,247 | B2* | 3/2017 | Bolene | G06Q 10/0833 |
| 9,971,874 | B2 | 5/2018 | Jafari et al. | |
| 10,529,044 | B2* | 1/2020 | Thompson | G16H 20/13 |
| 10,558,830 | B2* | 2/2020 | Havas | G06K 7/10386 |
| 10,588,823 | B1* | 3/2020 | Arora | A61J 3/074 |
| 2003/0164401 | A1* | 9/2003 | Andreasson | G07F 11/002 235/385 |
| 2004/0008123 | A1* | 1/2004 | Carrender | G06K 19/07749 340/8.1 |
| 2004/0193020 | A1* | 9/2004 | Chiba | A61B 5/07 600/300 |
| 2006/0289640 | A1 | 12/2006 | Mercure et al. | |
| 2007/0086625 | A1* | 4/2007 | Polli | G01N 21/359 382/115 |
| 2007/0237719 | A1 | 10/2007 | Jones et al. | |
| 2008/0303638 | A1* | 12/2008 | Nguyen | G06F 19/3462 340/10.42 |
| 2009/0149839 | A1* | 6/2009 | Hyde | A61B 5/14539 604/890.1 |
| 2009/0294521 | A1* | 12/2009 | de la Huerga | A61J 1/035 235/375 |
| 2010/0049363 | A1* | 2/2010 | Ratnakar | G06F 19/3462 700/236 |
| 2010/0147941 | A1* | 6/2010 | Silverbrook | G06Q 20/3674 235/375 |
| 2010/0324936 | A1* | 12/2010 | Vishnubhatla | G16H 50/70 705/3 |
| 2011/0009715 | A1* | 1/2011 | O'Reilly | A61B 5/07 600/302 |
| 2011/0304131 | A1* | 12/2011 | Zhou | G16H 20/13 283/74 |
| 2012/0278096 | A1* | 11/2012 | Holness | G16H 20/10 705/2 |
| 2013/0073312 | A1 | 3/2013 | Thompson et al. | |
| 2015/0343144 | A1* | 12/2015 | Altschul | A61B 5/01 604/503 |
| 2016/0292386 | A1 | 10/2016 | Finkelstein et al. | |
| 2016/0354283 | A1 | 12/2016 | Cho et al. | |
| 2017/0032101 | A1* | 2/2017 | Skoda | G06F 19/3456 |
| 2017/0098058 | A1* | 4/2017 | McCullough | A61M 5/31568 |
| 2017/0161439 | A1* | 6/2017 | Raduchel | H04W 12/06 |
| 2017/0213010 | A1* | 7/2017 | Sucilla | H04L 9/3226 |
| 2017/0235916 | A1* | 8/2017 | Woodyear | G06F 19/326 705/2 |
| 2017/0296436 | A1 | 10/2017 | Ziv et al. | |
| 2018/0132784 | A1 | 5/2018 | Euliano et al. | |
| 2018/0357387 | A1* | 12/2018 | Deus | G16H 20/13 |
| 2019/0035499 | A1* | 1/2019 | Daya | G16H 40/67 |
| 2020/0080980 | A1* | 3/2020 | Clark-Joseph | G01N 21/25 |
| 2020/0098460 | A1* | 3/2020 | Banks | G06K 7/1417 |
| 2020/0111556 | A1* | 4/2020 | Schmidlin | A61M 5/142 |

OTHER PUBLICATIONS

P. Bellagente, et al., The "Smartstone": using smartphones as a telehealth gateway for senior citizens, ScienceDirect, IFAC—PapersOnLine 49-30 (2016) 221-226 [retrieved Aug. 27, 2018].
Prepared for The Kaiser Family Foundation by: The Health Strategies Consultancy LLC, "Follow the Pill: Understanding the U.S. Commercial Pharmaceutical Supply Chain", Mar. 2005.
S. Bobba, et al., "eMedicare: mHealth solution for Patient Medication Guidance and Assistance", 2016 International Conference on Signal Processing, Communication, Power and Embedded System (SCOPES) (2016) [retrieved Mar. 13, 2019].
Proteus Digital Health, Otsuka and Proteus® Announce the First U.S. FDA Approval of a Digital Medicine System: Abilify MyCitee® (aripiprazole tablets with sensor), Press release (2017), downloaded on Mar. 13, 2019 from https://www.proteus.com/press-releases/otsuka-and-proteus-announce-the-first-us-fda-approval-of-a-digital-medicine-system-abilify-mycite/ Nov. 14, 2017.

* cited by examiner

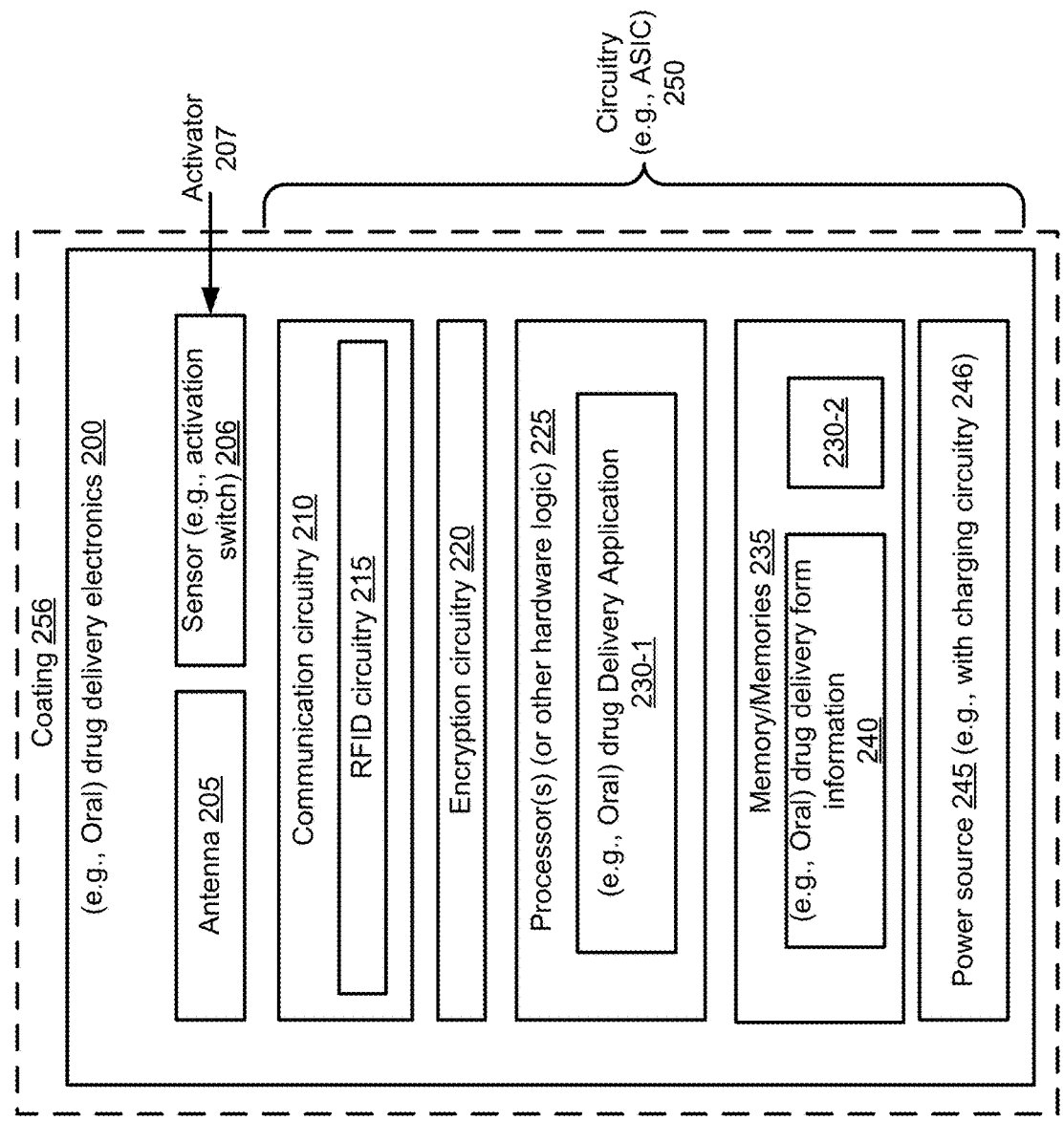
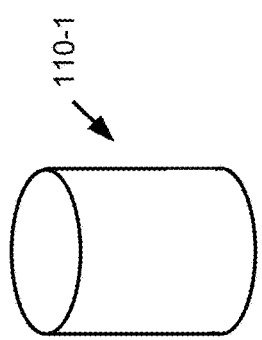
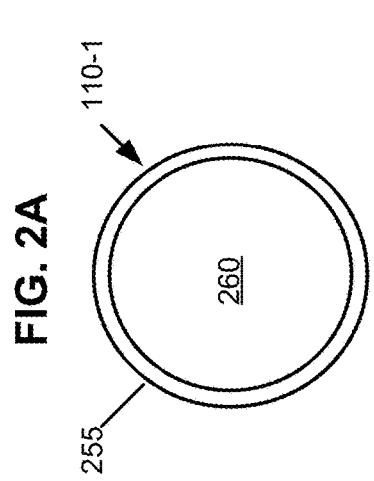
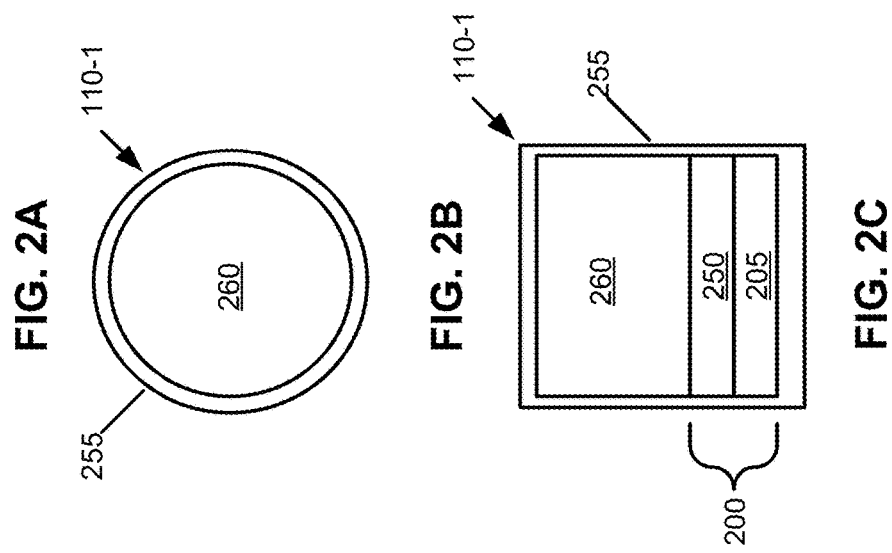

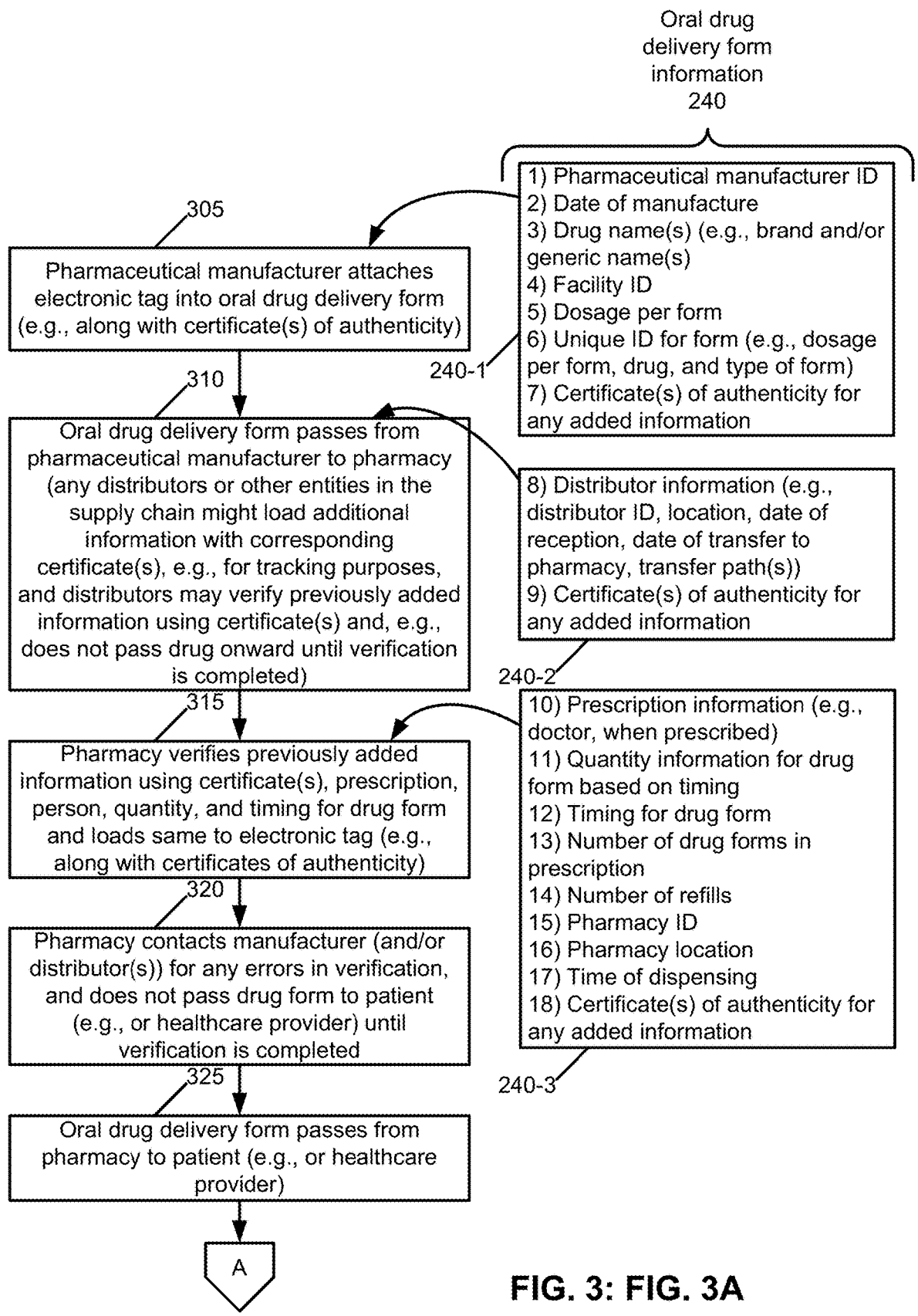
FIG. 3: FIG. 3A

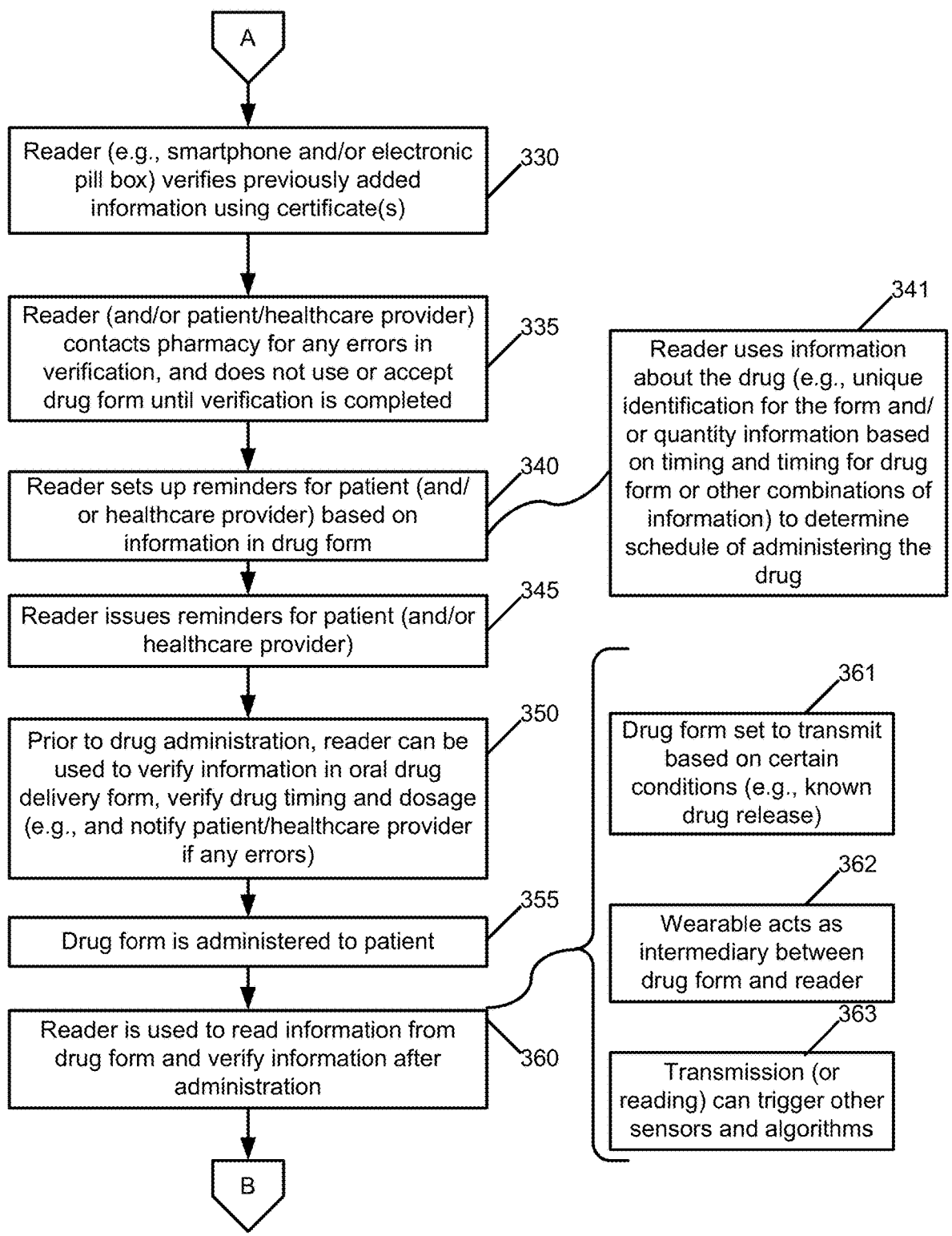
FIG. 3: FIG. 3B

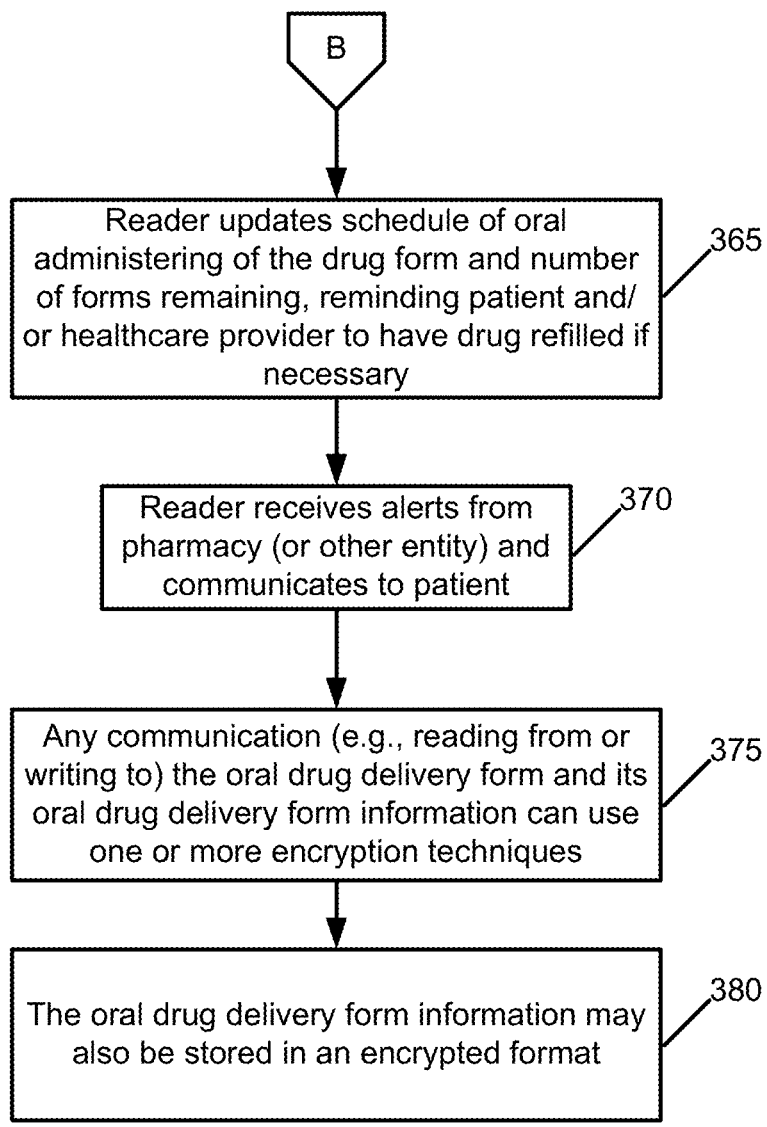
FIG. 3: FIG. 3C

ELECTRONICS MINIATURIZATION PLATFORM FOR MEDICATION VERIFICATION AND TRACKING

BACKGROUND

This invention relates generally to medicine delivered via an oral drug delivery form such as a pill and, more specifically, relates to electronics miniaturization platform for medication verification and tracking.

In order to properly administer medication, the medication should be taken at the correct dose and the correct time. Furthermore, it is beneficial to ascertain that this is the correct medication for the correct person, and it is important to verify medication is taken. This is a challenge for some persons who are elderly, with certain diseases, and the like.

Even for "normal" patients, it can be difficult to know when or whether drugs have been taken, particularly if there are multiple drugs with multiple doses. One common way to address this is to use multiple pill organizers, such as one for the morning and one for the evening, and placing drugs in the pill boxes by day of the week. That is, each of the pill organizers usually has a single row of compartments, one compartment for each day of the week, and the pills can be placed into their corresponding days. There are more complex versions, however, with two or three or four rows of compartments per day of the week, which can add a time element for each row. Even with these extra precautions, a patient could take a pill out of a compartment, put it on the counter or in his or her pocket, and forget to take the pill. This is a difficult situation to rectify.

Additionally, there have been a spate of drug recalls lately, for instance due to cancerous substances in blood pressure medication. From a patient standpoint, these can be difficult to learn about, and even if the patient does hear about a recall, the patient then has to do all or most of the work in determining whether their drug was manufactured by the particular manufacturer with the recall. This is particularly true for generic drugs, which may have multiple manufacturers. Even if there is one manufacturer of the drug, perhaps there are multiple manufacturing locations for that manufacturer, and only some of the locations might be affected by a recall.

SUMMARY

This section is meant to be exemplary and not meant to be limiting.

In an exemplary embodiment, a drug delivery form is disclosed. The drug delivery form includes a drug and electronics. The electronics includes one or more memories having drug delivery form information. The drug delivery form information includes information about the drug and about at least part of a supply chain from manufacture of the drug delivery form to a current location in the supply chain. The electronics also includes communication circuitry configured to read data from and write data to the drug delivery form information in the one or more memories.

In another exemplary embodiment, an apparatus is disclosed. The apparatus includes one or more memories having computer readable code, and one or more processors. The one or more processors, in response to retrieval and execution of the computer readable code, cause the apparatus to perform operations including communicating with a drug delivery form comprising a drug and drug delivery form information. The drug delivery form information includes information about the drug and about at least part of a supply chain from manufacture of the drug delivery form to a current location in the supply chain. The one or more processors, in response to retrieval and execution of the computer readable code, cause the apparatus to perform operations including reading data from or writing data into the drug and drug delivery form information.

A further exemplary embodiment is a method including receiving data at a computer system about a patient from one or more sensors, at least one of the sensors comprising a drug delivery form comprising a drug, electronics configured to contain information about the drug and about at least part of a supply chain, and communication circuitry configured to read data from and write data to the oral drug delivery form information. The data comprise at least information from the drug delivery form. The method includes performing by the computer system computational analysis on the data to determine one or more actions to be performed based on the patient's current status as defined by the data. The method includes performing by the computer system the determined one or more actions.

In another exemplary embodiment, an apparatus is disclosed. The apparatus includes one or more memories having computer readable code, and one or more processors. The one or more processors, in response to retrieval and execution of the computer readable code, cause the apparatus to perform operations including receiving data at a computer system about a patient from one or more sensors, at least one of the sensors comprising a drug delivery form comprising a drug, electronics configured to contain information about the drug and about at least part of a supply chain, and communication circuitry configured to read data from and write data to the oral drug delivery form information. The data comprise at least information from the drug delivery form. The one or more processors, in response to retrieval and execution of the computer readable code, cause the apparatus to perform operations including performing by the computer system computational analysis on the data to determine one or more actions to be performed based on the patient's current status as defined by the data, and performing by the computer system the determined one or more actions.

In a further exemplary embodiment, a computer program product includes a computer readable storage medium having program instructions embodied therewith. The program instructions are executable by an apparatus to cause the apparatus to perform operations comprising: communicating with a drug delivery form comprising a drug and drug delivery form information, the drug delivery form information comprising information about the drug and about at least part of a supply chain from manufacture of the drug delivery form to a current location in the supply chain; and reading data from or writing data into the drug and drug delivery form information.

In a further exemplary embodiment, a computer program product includes a computer readable storage medium having program instructions embodied therewith. The program instructions are executable by an apparatus to cause the apparatus to perform operations comprising: receiving data at a computer system about a patient from one or more sensors, at least one of the sensors comprising a drug delivery form comprising a drug, electronics configured to contain information about the drug and about at least part of a supply chain, and communication circuitry configured to read data from and write data to the oral drug delivery form information, the data comprising at least information from the drug delivery form; performing by the computer system computational analysis on the data to determine one or more actions to be performed based on the patient's current status as defined by the data; and performing by the computer system the determined one or more actions.

BRIEF DESCRIPTION OF THE SEVERAL VIEWS OF THE DRAWINGS

FIG. 2A is an example of an (e.g., oral) drug delivery form;

FIG. 2B is a top, cutaway view of the example of the (e.g., oral) drug delivery form from FIG. 2A;

FIG. 2C is a side, cutaway view of the example of the (e.g., oral) drug delivery form from FIG. 2A;

FIG. 2D is an example of (e.g., oral drug) delivery electronics in the example of the oral drug delivery form of FIG. 2C;

FIG. 3 is split into FIGS. 3A, 3B, and 3C and is a flowchart of a method for implementing and using an electronics miniaturization platform for medication verification and tracking.

DETAILED DESCRIPTION

Figure 1A:
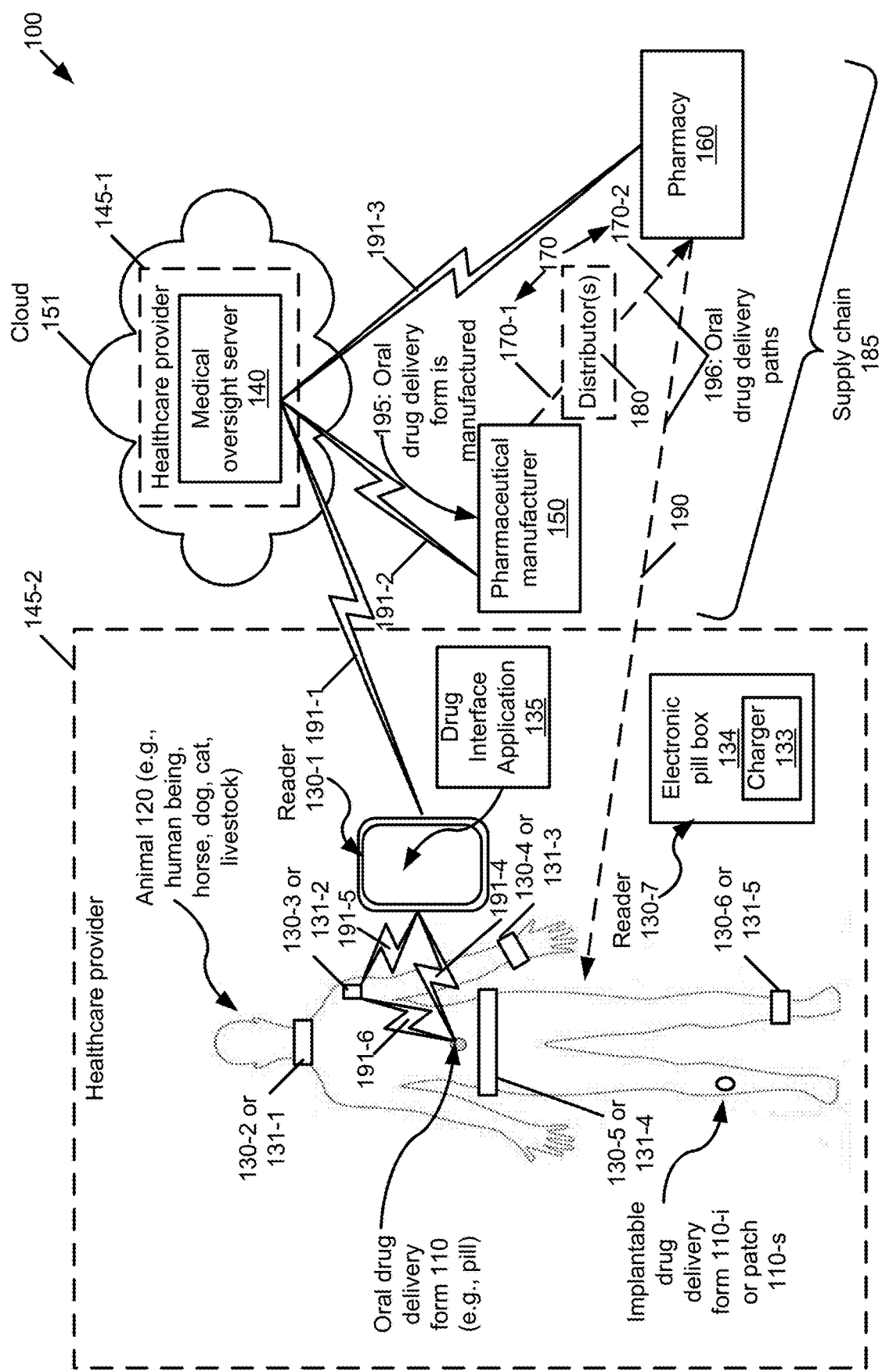
FIG. 1A is a block diagram of an exemplary system implementing electronics miniaturization platform for medication verification and tracking.

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

For ease of reference, the rest of this disclosure is divided into sections.

I. Overview

This section provides an overview of the exemplary embodiments. In order to address the problems described above, the systems and techniques described herein provide technical solutions to the same. For instance, in order to allow better medicine and verification tracking and correct problems with such, exemplary embodiments herein use electronics to track a unique identifier in each pill and use the electronics to link to correct medication, correct person, and correct timing of medication and use sensor(s) to verify medication is properly taken. The electronics and methods herein may also provide data storage and provide feedback to a user, a patient, a medical professional, insurance companies, and/or others with reason to track medications for a patient. A user could be, for example, a guardian of a minor or a senior citizen.

As an overview, certain exemplary embodiments use unique low cost and miniaturized electronics with identifiers that are appropriate for medication taken by a patient and can verify the medication and the prescription is valid for this patient. The verification may also include that the medication has authentication (also called verification) based on manufacturer (e.g., supplier) and a corresponding unique identifier, and encryption of the same. Exemplary embodiments may link each of these to patient needs per doctor or healthcare professional and appropriate monitoring requirements from a pill bottle, or a pill box, or from another electronic sensor(s) or diagnostic signal and with an option for verified consumption. The verified consumption may be performed by a signal from a stomach of person or other animal receiving the medication or from another body location sensor(s). This may be performed via an electronic signal from low cost and miniaturized electronics inside the body (e.g., in an oral drug delivery form or another sensor or diagnostic signal from physiological measurement from the body) to tracking electronics such as a smart watch or phone or other reader.

There is also an option of further medication dosage verification based on release of medication and bio-marker or bio-tag tracking via bio-diagnostic or sensor signal monitoring to validate effectiveness of the medication with associated data signal or sensor data providing effectiveness data feedback. For instance, urinalysis or blood or fluid testing for biomarkers such as protein, beta-amyloid, alpha-synuclein and tau or other bio-markers for neurodegenerative diseases like Alzheimer and Parkinson disease or glucose and cholesterol tracking for diabetes and cardiovascular diseases or creatinine, protein and nitrite for kidney disease or onco-nephrology. In addition, other localized biosensors may be used for local bio-sensing or for inflammation sensor monitoring. Complimentary physiological sensors associated with the medication and type of sensing such as monitoring of chronic diseases with motion, force, gait, grip strength, tremor, or other combinations of sensors could also be used for monitoring patients health, drug efficacy, drug effectiveness and drug dose/consumption validation.

Furthermore, linking data streams of medication, patient history, data stream of timing of medication history, dosage level, timing of consumption with verification of consumption and verification of effectiveness of medication based on one or more biosensors or diagnostic sensors and/or other physiological sensors and their respective data or data streams may be performed. Similarly, data trending and/or use of machine learning (e.g., artificial intelligence (AI)) or other algorithms may be performed against classification for disease, patient information and trending for validation, effectiveness and prediction/recommendations for patient to care giver, doctor or patient, family member or others as selected for use of this technology.

Although emphasis herein is place on using the electronics miniaturization platform and corresponding methods for human beings, the platform and methods may be used for other animals such as cats, dogs, horses, and livestock. For animal tracking of other animals, a collar for dogs and cats can be used to track pill confirmation, receive signals from the stomach to outside the body, and the like. Other wearables such as patches or sensors embedded in ears or other options might be used for other animals such as horses or livestock.

For human beings, in exemplary embodiments, sensor data signal transmission may be used when stomach fluids activate a sensor integrated with the medication from a stomach location to an external reader activated by radio frequency (RF), where the transmission may be activated using for instance an Mg (magnesium) battery activated by stomach acids or alternate electronics energy source. The signal between the stomach and the external sensor may be by ultrasound, RF or alternate signal.

There may be a closed loop option for medication effectiveness with biosensor(s) bio-diagnostics, health sensor(s), use of classifiers per disease/use or application condition, artificial intelligence (AI), automated closed loop sensing and/or additional electronic drug delivery, and the like. The following are examples for illustration where the multiple sensors and drug delivery dosages may be all electronically controlled in cavities and activated, or may include a combination of sensing and coatings on oral dosages that are dissolved over time.

1. For closed loop sensing and drug delivery and verification, we can use ultra-small sensors such as functionalized surfaces to sense specific biomarkers. These sensors can be outside the body, e.g., on a skin patch that is worn for one or two weeks and sense glucose level in sweat with many sensors activated for a reading at periodic times. Corresponding electronic signals may be sent to patient for oral medication or to electronic drug delivery devices that deliver a drug or drugs from an electronic system.

2. There can be a sensor in a pill that is swallowed and tracked through the intestinal system and activated (via the sensor) with additional dosage of drug release over time such as coatings that are dissolved over time.

3. There can be an implanted sensor and drug delivery/verification system such as for a knee implant that has many integrated sensors, and drug depositories that can be activated on demand or based on timing of the electronic micro-system. In this case, the sensor may look for inflammation by the implant and if the sensor detects inflammations such as biomarker IL-8, and/or other bio markers, then a localized drug release may be made such as an antibiotic using a signal from the sensor and a drug release signal, which is a closed loop electronic signal reading. This may include a corresponding action/and verification of drug release, and may be performed one or more times until inflammation signals are reduced due, e.g., to antibiotic doses released locally. Note that one can have tens or thousands of these miniaturized sensors and drug release cavities, each sealed and useable/opened by time or on demand, with, e.g., closed loop monitoring over long periods of time such as weeks, months, years.

II. Description of Exemplary Systems

Now that an overview has been provided, additional detail is provided. Turning to FIG. 1A, this figure is a block diagram of an exemplary system 100 implementing electronics miniaturization platform for medication verification and tracking. In this example, there is an animal 120 that has swallowed an oral drug delivery form 110. The oral drug delivery form 110 may be, for instance, a pill, tablet, capsule, pastille, lozenge, or any other item that will deliver a drug orally. As used herein, a "drug" is considered to be any medication or combinations of medications. The oral drug delivery form 110 may also include binders, enteric coatings, inactive ingredients, and other ingredients as is known in drug manufacturing. The animal 120 in this example is a human being, but as previously described, other animals such as a horse, a dog, a cat, or livestock could be used.

The oral drug delivery form 110 is an electronics miniaturization platform that has wireless capabilities. In one example, there is a reader 130 having a drug interface application 135 in the reader. There are many possibilities for the reader, such as a smartphone (see reader 130-1), a collar (see reader 130-2), a patch (see reader 130-3), a wristband or smartwatch (see reader 130-4), a belt or belt buckle (see reader 130-5), or an ankle band (see reader 130-6).

In another example, the reader 130-1 (such as the smartphone shown or another device such as an electronic pill box 134 or laptop) reads information from a wearable 131, which itself has read the information from the oral drug delivery form 110. For instance, in a hospital situation, a wristband as wearable 131-3 could be used and gather information from one or multiple oral drug delivery forms 110, and staff in the hospital could use the reader 130-1 to determine which forms 110 were administered, e.g., and when (along with other information described below). The wearables 131 can include the following as examples: a collar (see wearable 131-1), a patch (see wearable 131-2), a wristband or smartwatch (see wearable 131-3), a belt or belt buckle (see wearable 131-4), or an ankle band (see wearable 131-5). Many other options such as implantable or alternate biosensing, bio-diagnostics, physiological sensor systems and/or drug delivery/verification integrated electronic systems are possible.

For ease of reference, the readers 130 and the wearable 131 will be referred to by their corresponding devices. For instance, the reader 130-1 will be referred to as smartphone 130-1, and the reader 130-3 (or wearable 131-2) will be referred to as patch 130-3 (or patch 131-2).

The oral drug delivery form 110 communicates via wireless link 191-4 to the reader 130 such as smartphone 130-1. The oral drug delivery form 110 may also or alternatively use the wireless link 191-6 to the patch 131-2, which then communicates via wireless link 191-5 to the smartphone 130-1. For clarity, the wireless links 191-5 and 191-6 are the only wireless links 195 shown between a wearable 131 and the oral drug delivery form 110 and also the reader 130.

It is noted that reference 131 may also indicate sensors, such as ECG, PPG, heart rate, heart rate variability, blood pressure, and other sensors. ECG (electrocardiography) sensors measure the bio-potential generated by electrical signals that control the expansion and contraction of heart chambers. PPG (photoplethysmography) sensors use a light-based technology to sense the rate of blood flow as controlled by the heart's pumping action. Also note often a PPG-type sensor using a clip-on end of a finger is used with an IR (infrared) sensor to monitor oxygen level in blood. The data from these may be combined with the pill information, as described below.

The exemplary embodiments provide tracking for medications. As reference 195 indicates, the oral drug delivery form 110 is manufactured by a pharmaceutical manufacturer 150. The oral drug delivery form 110 then passes (via path 170, which may be split into two paths 170-1, 170-2) to the pharmacy 160. The pharmacy 160 then passes (that is, dispenses) the oral drug delivery form 110 to the animal 120 via path 190. There typically are distributor(s) 180 involved between the pharmaceutical manufacturer 150 and the pharmacy 160. If these distributors 180 are involved in the tracking, then path 170 is split into path 170-1 between the pharmaceutical manufacturer 150 and the distributor 180, and into path 170-2 between the distributor 180 and the pharmacy 160. Reference 196 points out that there are multiple possible oral drug delivery paths 196. The oral drug delivery paths 196 and the corresponding entities 150, 180, and 160 may be considered to be a supply chain 185 for particular drugs, which ends at and may include the animal 120. Each drug may have its own supply chain 185. If there are other possible oral drug delivery paths 196 and parts of the supply chain 185 not shown in FIG. 1A, these may be added to the system 100.

At each of these entities in the paths 196 and the supply chain 185, information may be added to the oral drug delivery form 110. This is described in more detail below.

The reader 130-1 has a drug interface application 135 that may provide certain functions, as described below. The reader 130-1, pharmaceutical manufacturer 150, and the pharmacy 160 (and the distributor 180) may communicate via respective wireless links 191-1, 191-2, and 191-3 with a medical oversight server 140. This is an example of a "centralized" implementation, where one location contains information about the oral drug delivery form 110 and its paths 196 to the animal 120. The medical oversight server 140 may be, for instance, at a healthcare provider 145-1, which provides healthcare for the animal 120. The medical oversight server 140 may be located in the cloud 151. In other examples, the medical oversight server 140 is located in a network that is not the cloud 151. The medical oversight server 140 may be located in or wholly or partially controlled by a government organization, such as the Centers for Disease Control (CDC). For instance, the CDC may determine that a particular drug is contaminated and may alert the medical oversight server 140, which can then alert the other elements in the supply chain and also the animal 120 (and/or the healthcare provider 145 such as a veterinarian).

In other examples, the system 100 may be distributed, such that each entity in the supply chain is connected to other elements only through the paths 196. In the example of drug contamination, the CDC may alert the pharmaceutical manufacturer 150, which would then disseminate this information to the distributor 180, which then disseminates the information to the pharmacy 160 and so on to the animal 120 and/or healthcare provider 145.

The healthcare provider 145 may be a physician's office or network, a hospital, a veterinarian or veterinarian network, as examples. The healthcare provider 145-2 may be a physician's office, hospital or senior care facility or veterinarian, for instance, which has the animal 120 under its care.

The charger 133 is a device that might be used in some scenarios. For embodiments where the oral drug delivery form 110 contains a chargeable power source, the charger 133 acts to charge the oral drug delivery forms 110 via known wireless charging techniques. The charger 133 may be implemented as part of the electronic pill box 134, may be standalone, or may even be implemented as part of a reader 130.

The electronic pill box 134 is another device that might be used in some scenarios. This example has charging capability, but the electronic pill box 134 may have other functions in addition or alternative to charging. For instance, the electronic pill box 134 might act as a smart device that can perform some or all of the operations attributed to the reader 130, such as reminders to a patient and medication logging and communication with a healthcare provider 145. The electronic pill box 134 may therefore be or incorporate a reader 130, and is consequently illustrated as reader 130-7.

While the primary emphasis herein is placed on an oral drug delivery form 110 (that is, something swallowed), other delivery options are possible. For instance, the drug delivery form 110 could be implantable and be an implanted drug delivery form 110-i. The implantable drug delivery form 110-i could be a drug pump, a subcutaneous solid implant, solid implant, intrauterine devices (IUDs) and intravaginal rings (IVRs), and the like. Another option is the drug delivery form 110 could be applied to the surface of the animal 120 (e.g., to a shaved area) and be a patch drug delivery form 110-p, which could be a surface skin patch or bandage-like device as examples.

Figure 1B:
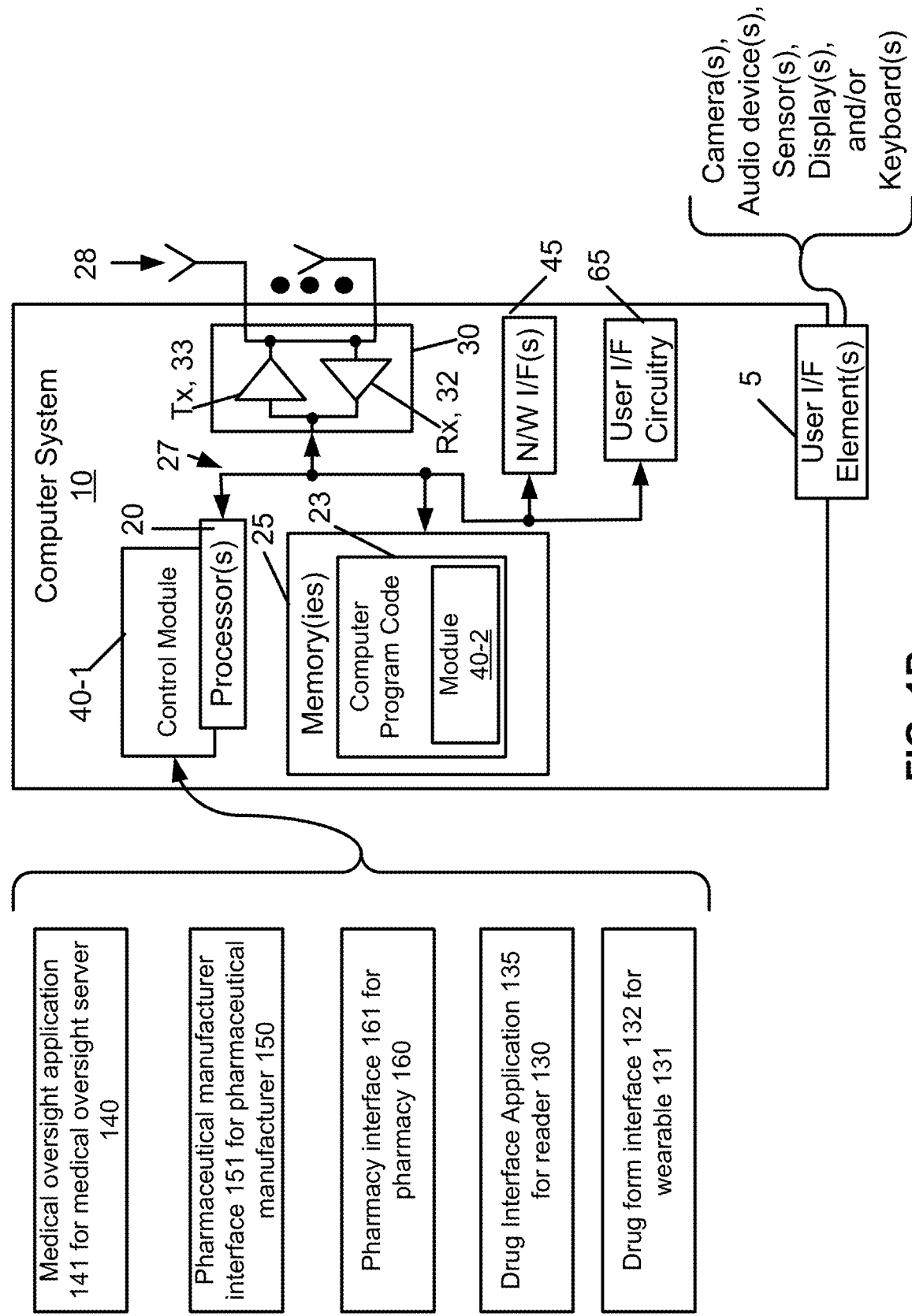
FIG. 1B is a block diagram of an exemplary computer system that may be used in multiple devices from FIG. 1A.

Turning to FIG. 1B, this figure is a block diagram of an exemplary computer system 10 that may be used in multiple devices from FIG. 1A. The computer system 10 includes one or more processors 20, one or more memories 25, one or more transceivers 30, one or more network (N/W) interfaces (I/F(s)) 45, and user interface circuitry 65, interconnected through one or more buses 27. Each of the one or more transceivers 30 includes a receiver, Rx, 32 and a transmitter, Tx, 33. The transceivers may use any applicable protocol, such as wireless fidelity (Wi-Fi), Bluetooth, near field communication (NFC), and/or cellular protocols such as 4G (fourth generation) or 5G (fifth generation). The one or more buses 27 may be address, data, and/or control buses, and may include any interconnection mechanism, such as a series of lines on a motherboard or integrated circuit, fiber optics or other optical communication equipment, and the like. The one or more transceivers 30 are connected to one or more antennas 28. The one or more memories 25 include computer program code 23.

The computer system 10 includes a control module 40, comprising one of or both parts 40-1 and/or 40-2. The control module 40 causes the computer system 10 to perform the operations described above that are performed herein by the individual devices. The control module 40 may be implemented in a number of ways. The control module 40 may be implemented in hardware as control module 40-1, such as being implemented as part of the one or more processors 20. The control module 40-1 may be implemented also as an integrated circuit or through other hardware such as a programmable gate array. In another example, the control module 40 may be implemented as control module 40-2, which is implemented as computer program code 23 and is executed by the one or more processors 20. For instance, the one or more memories 25 and the computer program code 23 may be configured to, with the one or more processors 20, cause the user computer system 10 to perform one or more of the operations as described herein. It should also be noted that the devices shown in the user computer system 10 are not limiting and other, different, or fewer devices may be used. For instance, a wired N/W IF 45 might not be necessary if only wireless networking via one or more transceivers 30 is used instead.

The user interface circuitry 65, which may or may not be implemented, communicates if implemented with one or more user interface elements 5, which may be formed integral with the user computer system 10 or be outside the user computer system 10 but coupled to the user computer system 10. The user interface elements 5 include one or more of the following: one or more camera(s); one or more audio device(s) (such as microphone(s), speaker(s), and the like); one or more sensor(s) (such as GPS sensor(s), fingerprint sensor(s), orientation sensor(s), and the like); one or more displays; and/or one or more keyboards. This list is not exhaustive or limiting, and other, different, or fewer elements may be used.

In terms of exemplary implementations for different devices in FIG. 1A, the control module 40 can be implemented as one of the following for the computer system 10 of the corresponding device: a medical oversight application 141 for medical oversight server 140; a pharmaceutical manufacturer interface 151 for pharmaceutical manufacturer 150; pharmacy interface 161 for pharmacy 160; drug interface application 135 for reader 130; or a drug form interface 132 for wearable 131. It is noted that the pharmaceutical manufacturer 150, distributor 180, pharmacy 160, and any other entity that might add information to or read (e.g., and verify) information in the oral drug delivery form 110 would have some version of a reader 130, in order to access the information in the oral drug delivery form 110.

III. Examples of the (e.g., Oral) Drug Delivery Form 110

FIGS. 2A, 2B, 2C, and 2D provide examples of how the (e.g., oral) drug delivery form 110 might be implemented. FIG. 2A is an example of (e.g., an oral) drug delivery form 110-1, in this case a pill (but could be an implantable device). For ease of reference, the drug delivery form 110-1 will be assumed to be an oral drug delivery form. FIG. 2B is a top, cutaway view of the example of the oral drug delivery form 110-1 from FIG. 2A. In this example, the oral drug delivery form 110-1 comprises a coating 255 and a drug 260. The drug 260 includes one or more medications and might also include one or more binder(s), and/or one or more inactive ingredient(s). FIG. 2C is a side, cutaway view of the example of the oral drug delivery form 110-1 from FIG. 2A. This example shows the coating 255, the drug 260, and (e.g., oral) drug delivery electronics 200 comprising circuitry 250 and antenna 205. The example shows the antenna 205 being separate from the circuitry 250, but these also may be consolidated. The circuitry 250 may also be split into multiple modules if desired.

Turning to FIG. 2D, this figure is an example of oral drug delivery electronics in the example of the oral drug delivery form 110-1 of FIG. 2C. The oral drug delivery electronics 200 comprises the antenna 205, a sensor 206, and the circuitry 250. The circuitry 250 comprises the following: communication circuitry 210; encryption circuitry 220; one or more processors (or other hardware logic) 225; one or more memories 235; and a power source 245. The circuitry 250 may be an application specific integrated circuit (ASIC) or other hardware such as with field programmable gate arrays (FPGA), Erasable Programmable Read-Only Memory (EEPROM) or other electronics with supporting software programing to personalize the hardware for the needs of the patients. The circuitry 250 may also comprise one or both of the antenna 205 and the sensor 206. There is a coating 256 that might be used around some or all of the electronics 200.

The communication circuitry 210 comprises RF identification (ID) circuitry 210. The RFID circuitry 210 can be an ultra-small ID tag that is used for medication confirmation the pill was made by qualified manufacturer and can act to provide data security/encryption for private—secure communications with electronic reader, patient and patent care providers. It is noted that "/" placed between two different words may be interpreted as "and/or". For instance, "data security/encryption" may be interpreted as "data security and/or encryption". The RFID circuitry 210 is one example of circuitry that may be used to communicate between the oral drug delivery form 110 and other entities, such as the reader 130 and/or wearable 131. The drug verification signals pass through ingestion and stomach and can be scanned or be automatically sent for both humans and other animals. As described above, the signal can be from the stomach (or other location in the digestive tract) to a skin patch 131-3, belt 131-4, or other wearable 131 and then to a smart phone 130-1 or other reader 130. In this example, there might be use of ultrasound to outside the body and then RF to smart phone 130-1 or other reader 130. The communication circuitry 210 therefore is configured to communicate via ultrasound. There may also be use of RF to outside body and then a second RF signal (e.g., to boost the RF signal from inside the body) to a smart phone 130-1 or other reader 130. The RF may be used directed to the smart phone 130-1 or other reader 130, e.g., such as if the smart phone 130-1 or other reader 130 is within a certain (e.g., relatively close) proximity such as 2 to 15 cm to the oral drug delivery form 110 as the form 110 is in the animal 120. Closer distances often have higher efficiency for power transmission and for signal quality for given antenna sizes. The communication circuitry 210 is configured to provide the RF receiver(s) and transmitter(s) used for communication outside the body and communication during transit to the animal 120. The RFID circuitry is one way this can be implemented, as RFID circuitry can be powered based on outside RF signals, and can therefore at least power some or all of the circuitry 250 in response to reception of outside RF signals. It may be possible to solely use the RFID circuitry 215 to power the circuitry 250, but this depends on many factors. For instance, for shorter distance and large antenna, localized small power source can be adequate. For longer distances, smaller antenna, an added power source 245 may be needed. Also for implanted applications needing a long lifetime, external power sources are preferred.

The encryption circuitry 220 is used, e.g., to encrypt and decrypt communications using known techniques. For instance, the patient and care provider would have keys to ensure privacy of data and authorize data access and avoid data interference, theft or malicious interference. Although this is shown separately from the one or more processors 225, this may also be incorporated into the one or more processors 225.

The oral drug delivery application 230 performs various functions, including controlling the operation of the circuitry 250 and therefore the oral drug delivery electronics 200. The oral drug delivery application 230 also controls communication between the oral drug delivery form 110 and the outside world, and provides access to and writes information into and reads information from the oral drug delivery form information 240 (described in more detail below). The oral drug delivery application 230 may be implemented in a number of ways. The oral drug delivery application 230 may be implemented in hardware as (e.g., oral) drug delivery application 230-1, such as being implemented as part of the one or more processors 225. The oral drug delivery application 230 may be implemented also as hardware logic that is configured to perform the operations described herein. In another example, the oral drug delivery application 230 may be implemented as oral drug delivery application 230-2, which is implemented as computer program code and is executed by the one or more processors 225. For instance, the one or more memories 235 and the oral drug delivery application 230-2 may be configured to, with the one or more processors 225 (or other hardware logic), cause the oral drug delivery electronics 200 to perform one or more of the operations as described herein. The oral drug delivery application 230 may be implemented using both the oral drug delivery application 230-1 and oral drug delivery application 230-2. The one or more memories 235 may comprise both volatile and non-volatile memories, although typically at least the (e.g., oral) drug delivery form information 240 would be stored using writable but non-volatile memory. This however also depends on whether the power source 245 is able to continuously supply power (e.g., such that volatile memory could be used but retain its programming due to continuous power) or not.

The power source 245 may be a small battery, capacitor, or super capacitor, e.g., precharged outside the body with an electronic charge station for all pills. Such a station could be via the reader 130, an electronic pill box 134, or the like. The power source 245 can include charging circuitry to enable wireless charging of the power source 245. Wireless charging is known. Alternatively or additionally, the power source 245 can be battery activated inside a body such as from stomach acids for Mg-activated battery or being an $H_2O$-activated battery or the like. The power source 245 can be localized from the sensor/pill and/or it is possible to use wireless power transmission such as near field communications (NFC) to power the electronics, or some combinations of these.

The sensor 206 may be some type of activation switch. That is, the sensor 206 could be an activation switch that is activated by an activator 207 to send a signal, and the sensor 206 then works with communication circuitry 210, antenna 215, RFID circuitry 215, encryption circuitry 220, and power sources 245 to send the signal. Note the sensor 206 can be triggered by stomach fluids (e.g., acids, as an activator 207) to be activated. Alternate sensors could be triggered by other activators 207 based on location of the sensor 206. For a wearable patch, the activator 207 may be sweat; for an implanted sensor and drug delivery device, the activator 207 may be inflammation; and for a bio-sensor, the activator 207 may be a chemical that picks up a signal from IL-8 (Interleukin 8). The integrated sensor 206 may determine one or more doses of medication after oral consumption. Other options are possible.

FIG. 2D illustrates the use of RFID and encryption for personalized secure data transfer, storage, and the like. The electronics 200 can be sealed in a coating 256 such as a polymer coating, to survive minutes or hours for data transfer after ingestion. Materials such as Parylene (a trade name for a variety of chemical vapor deposited poly(p-xylylene) polymers used as moisture and dielectric barriers), polymer, or metal/ceramics such as Si, Al, Ni, Cu, Au, Pt and/or $Al_2O_3$, SiN, or other compatible materials/composites may be used for the coating 246 and its corresponding sealing. Additionally or alternatively, Methocel may be used with controlled thickness and/or dissolution rate for the coating 256. METHOCEL cellulose ethers are water-soluble polymers derived from cellulose. The METHOCEL product range encompasses methylcellulose and hydroxypropyl methylcellulose (hypromellose), each available in different grades, physical forms and a wide range of viscosities. These types of coatings 256 may allow the oral drug delivery form 110 to survive minutes or hours for data transfer after ingestion.

The examples herein therefore propose a structure of medication in a form like a pill (as an example), with an electronic tag, a communication device, possibly a battery/capacitor/energy device, with an antenna and a coating to dissolve that may be used to activate the device and send a signal. The coating may also be used to protect electronics. The wiring/electronics may be passed though body and disposed of, typically through sewage systems. In other exemplary embodiments, the wiring/electronics or portion of electronics can be configured to act as a vitamin/body supplement such as Zn, Mg, Fe, and the like that can also function as wiring/antenna, and the like.

The electronics size can be from about 50 $\mu m^3$ to less than 5 $mm^3$ (cube size, though the cube shape is merely exemplary) with costs estimated at around $0.005 to $0.05 depending on product application, patient needs, and the like. Electronics can be sealed using polymer coating and or metal/ceramic coatings as indicated above.

FIGS. 2A to 2D are similar in concept for use of implanted, on skin patch or electronic ingestible medication, as each uses similar methodology on medication or drug delivery. One exemplary difference of each of these electronic drug delivery devices relative to oral medication or oral medication with simple ID validation and consumption validation data signal, and including oral consumption of traditional pills, is that these electronic drug delivery devices may permit one or more doses to be released electronically. Note this would mean not having the oral pill manufactured, or having a pill box or having the other oral elements such as oral reader, and the like. Instead, the electronic drug delivery system would have an encapsulated drug dosage with one or, more likely, more than one drug dose, e.g., each separately contained and sealed, which could be electronically opened like using a fuse open, to permit the drug dose to be released based on sensor data, on demand release, automated timed release, or combinations therein. For instance, see the following for techniques that might be used, in conjunction with the examples herein, for providing this drug dosage release: U.S. Pat. No. 9,867,932; and U.S. Publication No. 2017/0291019.

IV. Exemplary Methods

Turning to FIG. 3, this figure is split into FIGS. 3A, 3B, and 3C and is a flowchart of a method for implementing and using an electronics miniaturization platform for medication verification and tracking. The blocks are assumed to be performed by computer systems at each of the entities in the method. The left-hand side shows operations in different blocks, and the right-hand side for FIG. 3A shows examples of what might be contained in the oral drug delivery form information 240 in an oral drug delivery form 110. This example uses a patient, a human being, as the animal 120, although the example is equally applicable or modifiable to other animals.

In block 305, the pharmaceutical manufacturer 150 attaches an electronic tag (as the oral drug delivery electronics 200) into an oral drug delivery form 110 (e.g., along with certificate(s) of authenticity). The oral drug delivery form information 240-1 might include the following: 1) Pharmaceutical manufacturer ID; 2) Date of manufacture; 3) Drug name(s) (e.g., brand and/or generic name(s)); 4) Facility ID; 5) Dosage per form; 6) Unique ID for the form; and/or 7) Certificate(s) of authenticity for any added information. The dosage per form is, e.g., an amount of medication in each form, such as 25 mg per pill. The facility ID is an identification identifying a facility under control of the pharmaceutical manufacturer 150 that manufactures the oral drug delivery form 110. The dosage per form could be, e.g., 25 mg per pill. The unique ID identifies the form 110, such as identifying the drug, dosage of form, and type of form. For instance, a capsule with acetaminophen at 325 mg/capsule should have an ID that is different from a pill with acetaminophen at 325 mg/pill.

Whenever the oral drug delivery form information 240 is described, there could be fewer, more, or different information. For example, the pharmaceutical manufacturer 150 could include a JPG (joint picture expert group) file showing the form 110, and/or other indicia on the form 110. Many pills can be identified by color and markings on the pill. This information could be used by a patient or healthcare provider 145 to further verify the medication. As an example, an oblong white pill with TV on one side and 7269 on the other side identifies this pill as carvedilol 25 mg, supplied by Teva Pharmaceuticals, USA. These are called imprint codes and all approved prescription and over-the-counter solid, oral dosage form medications in the U.S. are required by the Food and Drug Administration (FDA) to have a unique imprint. This also applies to biological drug products and homeopathic drug products, unless otherwise exempted in the FDA Code of Federal Regulations 206.7. Other information such as the type of form (e.g., pill, tablet, capsule, and the like), binders or other inactive ingredients, and the like may be added.

The certificate(s) of authenticity are used to verify the information is correct and from this particular pharmaceutical manufacturer 150. The other certificate(s) of authenticity describe below may be used for the entities writing the certificate(s) of authenticity into the oral drug delivery form 110. That is, they verify the information is correct and from this particular entity. Also, the verification may help ensure a drug is taken prior to drug expiration and may have a proper dosage level linked to prescription authorization (which may change over time) or if a drug lot has been recalled for safety, drug manufacturer or prescription-based controls.

In block 310, the oral drug delivery form passes from the pharmaceutical manufacturer 150 to the pharmacy 160. Any distributors 180 (or other entities in the supply chain) might load additional information with corresponding certificate(s), e.g., for tracking purposes, and distributors may verify previously added information using certificate(s). This is illustrated by the oral drug delivery form information 240-2, where one or more of the following might added: 8) Distributor information (e.g., distributor ID, location, date of reception, date of transfer to pharmacy, transfer path(s)); and 9) Certificate(s) of authenticity for any added information.

The distributor 180 can verify the information 240-1 previously added. The distributor 180 also typically does not pass the drug form onward until verification is completed. For example, the distributor 180 can report to manufacturer and FDA and/or care provider/insurance company.

In block 315, the pharmacy 160 verifies previously added information using certificate(s), and verifies the prescription, person, quantity, and timing for the drug form and loads same to the electronic tag (e.g., along with certificates of authenticity). The oral drug delivery form information 240-3 may include the following: 10) Prescription information (e.g., doctor, when prescribed, where prescribed); 11) Quantity information for drug form based on timing; 12) Timing for drug form; 13) Number of drug forms in prescription; 14) Number of refills; 15) Pharmacy ID; 16) Pharmacy location; 17) Time of dispensing; and 18) Certificate(s) of authenticity for any added information. As for the quantity information for drug form based on timing and the timing for drug form, this could be "take two times per day, in the morning and evening", and the quantity information is the "two times" and the timing is "per day, in the morning and evening". In this example, the pharmacy ID is the pharmacy company, and the pharmacy location is the street address of the pharmacy that gives the oral drug delivery form 110 to the patient (or to the healthcare provider 145). Many other options are possible. For instance, other material may be added, such as a signature of whoever picks up the prescription, and/or how the prescription was transferred (e.g., mail, in person), the phone number of the pharmacy or doctor, and the like.

In block 320, the pharmacy 160 contacts the pharmaceutical manufacturer 150 (and/or distributor(s) 180) for any errors in verification, and does not pass the drug form 110 to the patient (e.g., or healthcare provider 145) until verification is completed. In block 325, the oral drug delivery form 110 passes from the pharmacy 160 to the patient (e.g., or healthcare provider 145). That is, the pharmacy 160 dispenses the oral drug delivery form 110 to the patient or healthcare provider 145.

In block 330, a reader 130 (e.g., smartphone 130-1 and/or electronic pill box 134 as a reader 130-7) verifies previously added information using certificate(s). In block 335, the reader 130 (and/or the patient or healthcare provider) contacts the pharmacy 160 for any errors in verification, and does not use or accept the drug form 110 until verification is completed. In block 340, the reader 130 may set up reminders for the patient (and/or healthcare provider) based on information in the oral drug delivery form information 240. The reader 130 may use any information in oral drug delivery form information 240 for this determination, such as the reader 130 using (see block 341) information about the drug (e.g., unique identification in (6) for the form and/or quantity information based on timing in (11) and timing for drug form in (12), or other combinations of information) to determine a schedule of administering the drug.

In block 345, the reader 130 may issue one or more reminders for patient (and/or healthcare provider). For instance, if it is time to take a drug based on the timing for the drug form and the quantity information for the drug form based on the timing, such as it being evening and the patient has not yet taken a drug that should be taken twice a day, the reader 130 may alert the patient (or the healthcare provider 145). This alert may take many forms, such as being shown on a display, triggering an audible alarm, sending an email, some combinations of these, and the like.

In block 350, prior to drug administration, the reader 130 can be used (e.g., by the patient and/or healthcare provider 145) to verify information in oral drug delivery form, and verify drug timing and dosage. Any error can be communicated to the patient and/or healthcare provider 145. Such notification may take many forms, such as being shown on a display, triggering an audible alarm, sending an email, some combinations of these, and the like.

Assuming there is no error, or the error is corrected (e.g., the correct pill is selected instead of the other pill that was previously used), the drug form 110 is administered to the patient in block 355. Another option is illustrated by block 360, where the reader 130 is used to read information 240 from the drug form 100, and potentially verify information, after the oral drug delivery form 110 has been administered (e.g., swallowed). This operation allows the patient and/or the healthcare provider 145 to verify the pill was actually taken by the patient (e.g., instead of remaining on a counter or in a pocket).

As an example of block 360, the drug form 110 may be set to transmit (see block 361) based on certain conditions (e.g., known drug release). For instance, once the drug form's coating 256 is breached, the drug form 110 may be able to determine this and in response transmit data from the oral drug delivery form information 240, e.g., indicating the drug's name, unique ID, quantity information for the drug form based on timing, and timing for the drug form. The determination of the breach of the coating may be by using an Mg battery activated by stomach acids. Furthermore, the signal quality from stomach to reader can determine, e.g., using cognitive computing and machine learning, a trend and verify the signals are actually coming from the person intended and not from another individual or dropped into a cup or other liquid.

As previously described, the reader 130 may be used alone or used in conjunction with one or more wearables 131. In this embodiment, the wearable acts as intermediary between the drug form 110 and reader 130. See block 362.

The wearable 131 may automatically transmit (e.g., in response to receiving data from the oral drug delivery from 110) to the reader 130, or the wearable 131 may store information and the reader 130 can read that information at some future time.

Block 363 illustrates another example, where transmission (or reading) can trigger other sensors and algorithms. For instance, perhaps the animal 120 is in a hospital (for humans) and has just taken blood pressure medication. The transmission/reading might trigger an algorithm to track the patient's blood pressure over time. This would allow a doctor or nurse to determine the patient's response to the blood pressure medication.

Block 365 is another example, where a reader 130 updates a schedule of oral administering of the drug form and number of forms remaining, reminding patient and/or healthcare provider to have drug refilled if necessary.

Block 370 indicates another possibility, where the reader 130 receives alerts from pharmacy (or other entity such as the CDC or healthcare provider 145) and communicates the alerts to the patient (or healthcare provider 145). The alert could be that the drug form should not be used due to possible contamination or the like.

Block 375 also illustrates that any communication (e.g., reading from or writing to) the oral drug delivery form 110 and its oral drug delivery form information 240 can use one or more encryption techniques. That is, the data in the reading can be encrypted on one end of the communication (e.g., by the encryption circuitry 220 of the electronics 200 of the oral drug delivery form 110) and decrypted by the reader 130. Similarly, the data in the writing can be encrypted by the reader 130 and decrypted by the encryption circuitry 220 of the electronics 200 of the oral drug delivery form 110. Additionally, block 380 indicates that the oral drug delivery form information 240 may also be stored in an encrypted format.

Figure 4:
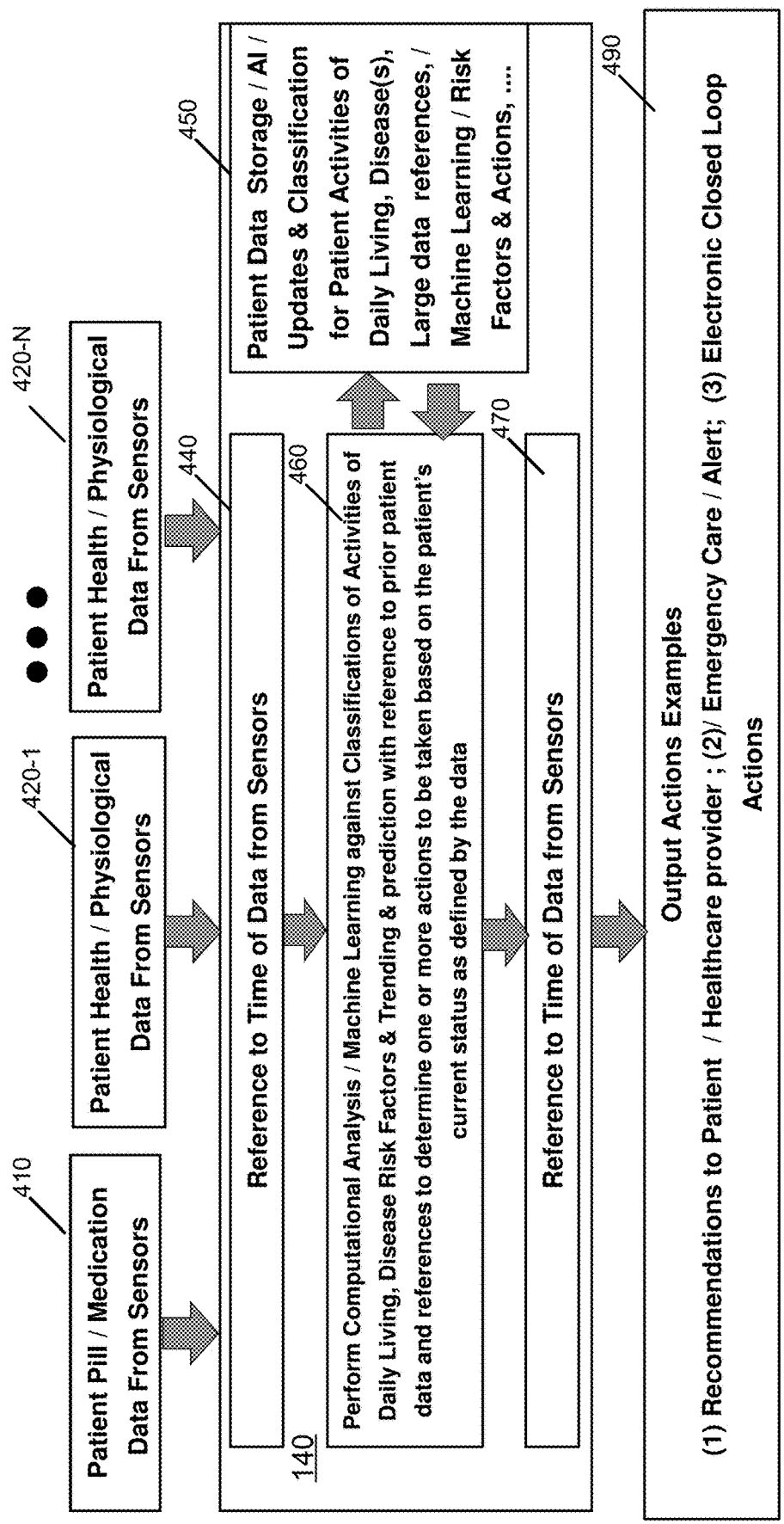
FIG. 4 is a flowchart that outlines the operations that a medical oversight server can provide in an exemplary embodiment.

Turning to FIG. 4, this figure shows a flowchart that outlines the operations that the medical oversight server 140 can provide in an exemplary embodiment. These operations are assumed to be performed by the medical oversight server 140, e.g., under control of the medical oversight application 141.

Regarding the medical oversight server 140, this server can receive data or other information from one or multiple sources with associated time relevant reference. Such data might include pill/medication data taken by the patient and comprising data from sensors (see block 410) such as the reader 130, and other patient health/physiological data from sensors 420-1 through 420-N (e.g., from N different sources). Such patient health/physiological data 420 could include health sensor information with appropriate contextual information about the data or information relative to patient references such as patient activity or motion level (e.g., whether sleeping/at rest; sitting/limited motions or sitting driving a car; active patient such as walking, running, or other active activity with sensor measurements such as but not limited to heart rate, respiration rate, ECG, EMG, motion sensors, force/pressure sensors, and the like). The patient health/physiological data from sensors 420 may also include data for other patient references such as indication(s) of patient cognitive state (such as during sleep or actively thinking/engaged), or the environment (temperature/humidity/and the like).

The medical oversight server 140 can analyze and learn from this data from a patient (e.g., a specific person) and, e.g., compare this data to that individual's history of data. The medical oversight server 140 may also compare this data to reference data. The medical oversight server 140 may additionally or alternatively perform a data trends comparison of this patient to other large data sets and/or reference data, which may provide risk factors or actionable limits beyond which lead to alarms, alerts, recommended interventions, awareness or communications of the data, trend and risk to the patient and/or care provider to permit appropriate action or care to be provided toward the benefit of the patient. The medical oversight server 140 may further (alternatively or additionally), depending upon the risk level to the patient, perform comparison of data such as from activities of daily living or medication levels taken versus physician-prescribed for said patient and outcome of action or inaction. If such comparison warrants it, an emergency (e.g., using 911) call may be made or some alternate action performed. Examples include but are not limited to providing care to the patient if the sensors detect one or more of the following: the patient has ingested excessive medications that might harm the patient; the patient is at risk of death due to, e.g., a car accident, fall or other injury; sensor(s) have detected a high probability that the patient has had a stroke (or other debilitating event, such as a myocardial infarction) and is at a high risk to their health with limited time to act to recover or risk permanent loss of neurological function and/or motor functions; or due to their age, chronic disease or other condition, sensor(s) detect an event which needs to be addressed or medication provided with urgency or risk impact to the individuals health and quality of life.

The medical oversight server 140 in block 440 of FIG. 4 references the received data 410 and 420 to time of the data, e.g., as reported by the sensors. That is, the data would contain or be marked with an added time stamp as reported by sensors for subsequent reference and analysis. In an exemplary embodiment, therefore, block 440 supports incoming sensor information with addition of time stamp for each sensor transmitting data. In particular, there could be a significant data stream of information that may be coming in from multiple sensors, e.g., depending on frequency of data updates from each sensor.

In block 460, the medical oversight server 140 performs computational analysis, such as using machine learning, against classifications of activities of, e.g., daily living, disease risk factors and (&) (alternatively or in addition) trending & prediction (alternatively or in addition) with reference to prior patient data and references to determine one or more actions to be taken based on the patient's current status as defined by the data. For instance, the output could be one or more patient or care giver actions to be taken would be based on the data when placed in context to risk to patient for those actions. Examples might include but are not limited to the following: (1) Data in safe range, no action; (2) Data shows marked change that is above or below target threshold and therefore warrant intervention or alarm or (3) Data suggest patient is at high risk of death and therefore emergency measures should be taken/time to actions is critical. Block 450 illustrates patient data storage, such as patient data/AI (artificial intelligence) information/ updates and classification for patient activities of daily living, disease(s), large data references/machine learning/ risk factors & actions, and the like. This storage may be accessed when the medical oversight server 140 performs its computational analysis in block 450.

Regarding block 470, this operation supports outgoing transmission of integrated sensor data with time stamps. It is noted that the amount of data that may be passed out of the system is typically reduced (relative to incoming data), e.g., to focus on data with time stamps where the outgoing data has relevance to the patient. For instance, sensor data trending might be meaningful such as being outside normal fluctuations or requiring patient or care giver intervention or action. There may be, e.g., 10 to greater than 1000 times less data out than data in, but the data out may include information to create context, including such items as time stamp and relevance to patient state, such as sleeping, active, cognitive state, and also vital signs or other sensor data relevant to the patient.

In block 490, based on the computational analysis performed by the medical oversight server 140 in block 460, the medical oversight server 140 performs one or more output actions. Examples of these include, but are not limited to, one or more of the following: (1) providing recommendations to patient/healthcare provider; (2) providing (e.g., or sending messages to cause) emergency care/alert; and/or (3) electronic closed loop actions (see the description above for these).

V. Additional Implementation Information

This section describes additional implementation information and provides further comments. The electronics drug form and methods herein provide actionable outcomes for drug delivery, may provide a consumption time stamp (e.g., taken by the reader 130, wearable 131, and/or the oral drug delivery form 110), may provide data/algorithm results to the patient, healthcare provider, health insurance/pharmacy/drug company, and can provide electronic record keeping.

For providing actionable outcomes for drug delivery, this may mean that if a drug is not taken by a patient at a correct time, an electronic message may be sent to patient or care provider as reminder. As another example, if the drug is taken by wrong person, a message may be sent. Other examples range from oral medications to fully electronic systems of sensors and an electronic drug release mechanism with body-worn patches or implanted micro-systems that sense and take action to release drugs form multiple cavities based on time activation, closed loop sense and feedback drug release or on demand systems as an alternate to oral medications.

As for provide data/algorithm results, in this case, a time stamp may be used with input data streams from multiple sensors and a link to classification of activities of the patient can be used with cognitive computing to provide trending and prediction of patient needs. These data and predictions may indicate all is well with small shifts in results due to aging and no urgency or action is needed. These data may, however, suggest the patient missed a medication or sensors indicate patient is at risk for stroke or underwent a stroke or other event that should be addressed by patient or healthcare provider with urgency. Other data, algorithms and learning could be that the drugs taken by patient over time are becoming ineffective due to dosage level or problem in a lot of a specific drug is defective and patient data from users of this drug for this lot are all showing indications of drug being ineffective. Additional examples are possible.

Furthermore, a method could include drug (e.g., with one or more medications) delivery comprising one or more of the following:

(1) Pill or capsule (e.g., oral drug delivery form 110) taken by oral means which can also include surface coating(s) for timed release after taken by oral means, such pill or capsule having electronic ID tag and sensor/electronics to send a signal (or signals) comprising validity of medication, patient match and time stamp and/or other data during consumption of the medication;

(2) Use of an electronic drug delivery device (e.g., oral drug delivery form 110) which may be taken orally with electronic signals given to release one or more doses of medications upon receipt of a signal or signals and with an option to have an integrated sensor to determine one or more doses of medication after oral consumption; and/or (3) Use of electronic drug delivery device (e.g., implantable drug delivery form 110-*i*) which can deliver a drug (comprising one or more medications) based, e.g., on external electronic signal receipt and/or an integrated sensor which activates one or more drug or medication dosage release(s) in or on a localized region of the body. This could be from an implanted electronic medical device attached to ab implant, under skin such as injected via needle to under skin, be a surface skin patch or bandage-like device worn for a period of time, such as minutes, hours or days.

In any or each of these cases, the important element of this innovation is trying to provide validation of medication/ID, correct patient/ID, timing of medication with tracking/record and opportunity to track, trend this information for proper care to patient for better quality of life. Additional Information from other health sensors which can provide additional data and options for further care to patient in case of risk level and potential for improved time to medication dose in case of timing urgency if there is high risk to patient or risk of death or other need, provide benefit in case these can benefit the patient.

As described in part above, an electronic system platform has been described that allows for the following:

(1) Medication tracking from source to patient, (2) Sensing and medication delivery confirmation potentially with a time stamp of at least delivery and possibly ingestion;

(3) An option of sensing environment from other sensors; and (4) Perform one or more actions based on (1) and/or (2) and/or (3) for drug release and subsequent monitor measurements, local data analysis and/or data transfer, remote data analysis and algorithms/actions, feedback or updates to the patient, healthcare provider, physician or healthcare person and/or hospital, health insurance, drug company/others.

Concerning (3), the option of sensing environment from other sensors, in this case, other physiological sensor(s) and environmental sensor(s) may be important for health monitoring and understanding if medication is needed. An example is a person at rest sitting or sleeping versus running or walking or driving a car can impact the options for medication if someone has Parkinson disease and tremors and on and off states with medication versus other disease and medications. Thus, use of other environmental sensors such as motion, temperature and heart rate monitoring are complimenting other sensors for medications or bio-markers and there may be an impact of appropriate actions if treating neurological motor function disorders like Parkinson Disease versus cardiovascular disease or diabetes with measurements on glucose.

It should be noted that the methodology can be standardized to work with multiple suppliers of drugs, and verified as an authentic drug and for the user with a unique ID (e.g., of the oral drug delivery form 110). The method can be customized for the patient by pharmaceutical company/drug maker, drug pharmacy/local store, hospital/health provider/user or patient. The information 240 can be linked to a smart phone or device reminder, robot, pill box or alternate means for timeliness of ingestion. For example, if a pill is not taken on time (e.g., within a certain time period), a reminder alert may be sent to the patient's smart phone or to a care giver. The system and methods provide electronic communication from outside a body to inside the body, which may be used to activate drug release and/or the system provides use of coatings and timed release for some methods. In particular, we have demonstrated electronic drug delivery in small microsystems where medications can be enclosed into small cavities and each sealed. If activated by a signal (for instance), each cavity seal can be opened, which permits a drug to be released locally. This could be system-implanted in knee replacement, and this could be a small electronic system implanted in a tumor with cancer for controlled drug dosage delivery releases from external control or with integrated sensors and closed loop feedback controls for sensing, drug delivery and measurements.

The system and methods may provide data streams/time stamps for trending, effectiveness monitoring, link to other sensors/bio sensors/closed loop actions. For instance, a data stream for a drug or drugs may be run through a classifier linked to a disease or issue, and having personal health and family history, and the classifier may use the data stream for trending and actions/predictions/recommendations. The data stream may contain, e.g., physiological sensor signal information from a patient that may be a bio-chemical reading such as from a biomarker and blood test or urine test or may be a physiological sensor reading such as from a wearable sensor on the body such as motion or force or grip strength sensor, or combination of sensors that provides information about the patient. The combination of these sensor signal streams provides valuable information of the patient such as wellness, disease detection and disease monitoring. A classifier may use this information in the following manners, as example. Use of these data streams and classification against activities the patient has in their daily routines can be understood and quantified and trended over time. Thus, for a person who goes from sitting to walking, their gait, their balance during walking, their opening a door, picking up a cup of coffee and other daily activities can be monitored by these wearable and non-wearable room sensors. Classification of the sensor data against these types of activities of daily living (ADL) can give us an understanding of the patient's health, the efficacy of drugs or medications they may take and how they change over time. From monitoring these data streams, we can adjust medications, understand their chronic disease progression and determine if the patient needs assistance, should consider alternative medications, may have cognitive abilities or impairments that could suggest that driving is no longer recommended or when tremors are on or off due to medications, and the like. Accordingly, actions or changes in drug or medications can be made.

There is also an option for added closed loop electronic drug release from an electronic wearable, implanted or ingested digital drug delivery system. In particular, we have demonstrated electronic drug delivery in small microsystems where medications can be enclosed into small cavities and each sealed. If activated by a signal, each cavity seal can be opened which permits a drug to be released locally. This could be system implanted in knee replacement, this could be small electronic system implanted in a tumor with cancer for controlled drug dosage delivery releases from external control or with integrated sensors and closed loop feedback controls for sensing, drug delivery and measurements.

The system:
1) Can support different drug types and quantities;
2) Can support different dosage levels;
3) Can support different timed release based on time of pill taking plus time per each different drug or multiple dosage for same drug;
4) Can support sensor-driven feedback loop for drug release; and/or
5) Can support on demand/external input for drug release.

As described in part above, a patient can ingest medications which will then, possibly through electronics sensing/coating dissolution (e.g., alternate pass collar for animals), send a signal for drug verification to outside the body such as to a belt, body sensor or smart phone/electronic tracker. Concerning the alternate pass collar, in this case, for an animal such as cat or dog, a collar could act to verify the animal has swallowed a medication based on the medication passing from their mouth to their stomach and in doing so having passed through the insider of their collar which could have electronic sensors identifying medications which have electronics that are detected as a medication passes through the collar. This is an alternative to stomach to external reader signal detection.

1) The signal from pill, drug or medication may include a time stamp for drug release (e.g., at which the drug release was known to have begun).
2) The signal can also trigger activation of other sensors. This may occur for a patient environment update (sleeping/resting, active walk, run, vertical, sitting, or other sensing data/results).
3) The signal from the pill can then be used to send another signal for drug release and further sensor readings/updates. For instance, the other signal could be from the pill to reader and from reader to other electronics is possible and most likely. Although if medication drug with multiple reading sensor and drug delivery system is ingested, one could have signal from ingested pill also activate additional drug release and/or sensor readings from the injected sensor/drug delivery device that was ingested. Note some of the demonstrations made have had over 100 drug filled cavities in small size such as <3 to 10 $mm^3$ volume (which is very small).
4) The signal can also be used to alert the patient, physician, healthcare provider, or the like of medication confirmation.
5) The signal can also drive a local (e.g., at the edge) data algorithm or alert levels or send some or all data to a smart device, or to the cloud for larger data analytic assessment. The signal may be used for data recording and tracking, e.g., with history of trends and for appropriate actions via the medical supply chain of health providers, insurance company, physician, nurse, family members, and the like.

Another option is to utilize other complimentary patient environment sensors to understand patient relevant information such as being at rest, sleeping, being active such as walking or running or having high stress level, and the like. Reference is made back to FIG. 1A where the reader 130 can be a reader such as a smart phone which can collect information from multiple sensors on the body at locations such as 131-4, 131-5, 131-6 or other locations on or in the body as well as from environmental sensors on the body or in the room, car, and the like. The reader 130 can act to integrate the data streams from these multiple sensors 131, such as bio sensors, drug monitoring, and/or verification sensors, and either locally or with cloud computing communications provide sensor data to classification analysis using application algorithms linked to user personalized needs, health monitoring and/or chronic disease monitoring. These analysis tools can provide cognitive insights and care back to the patient, healthcare provider and/or others. Based on patient needs, trends and insights, proper care and risks levels can provide guidance to patient and care provider to support patient care and quality of life improvements.

Note that environmental sensors may be temperature sensors, accelerometers for motion monitoring, ECG (Electrocardiogram), PPG, electronic stethoscope for heart rate, blood pressure and other sensors for vital signs, biosensors for fluid bio-marker detection or dosage validation, an added indicator with examples of a fluid sensor coming from urinalysis, blood testing, saliva, tear film, sweat or other body fluid and with data detection timing. These may be linked to algorithm and machine learning/artificial intelligence with frequency of tests as needed from milliseconds for some health sensors to multiple times a day if needed for other bio or health or physiological sensors such as but not limited to these sensors: non-wearable sensors, wearable sensors, implantable and/or noninvasive sensors, bio sensors or diagnostic sensors at home, in a clinic, hospital or combinations of such sensors/diagnostics or points of care or diagnostics. The data from these may be stored, trended, and/or maintained by a personalized health data system, smart phone, watch, cloud and/or their combinations and communicated to the patient, doctor, care provider, family based on patient needs and selection as appropriate for care and quality of life enhancement.

Drug release (as indicated by the oral drug delivery form 110) can trigger activation of other sensors of drug verification. This drug release refers to electronic drug delivery for drug release from a cavity by means of cavity seal opening and corresponding drug release. Drug release and other sensor readings may trigger closed-loop feedback for added actions, monitoring added sensors above or below targeted limits, alarms, recommendations, data collection or other data analyses, trigger algorithms providing output to user, or medical supply chain of health providers, insurance company, physician, nurse, family members, and the like.

The oral drug delivery form 110 that remains after passing through the body is expected to be bio compatible and disposable, and the environmentally safe byproducts can pass through body and be flushed/passed away in normal passage/waste.

Note, the confirmation and signal can also have a unique identifier linked to an implanted chip in person or pet, location/GPS (global positioning system) of medication consumption as well as time stamp and recording and information transfer to a reader and appropriate health professionals, patient, health care insurance, or local recorder, cloud, and the like.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A drug delivery form, comprising:
a drug; and
electronics comprising:
one or more memories having drug delivery form information, the drug delivery form information comprising information about the drug and about at least part of a supply chain comprising multiple entities from a manufacturer of the drug delivery form and at least to a pharmacy in the supply chain, wherein the information about at least part of the supply chain comprises information added by each of the multiple entities and information concerning the pharmacy that dispenses the drug delivery form to an animal, the information added by each of the multiple entities comprising one or more certificates of authenticity, the one or more certificates for a corresponding one of the entities used to verify the drug delivery form information and the corresponding added information is correct and is from the one entity that added the corresponding information; and
communication circuitry configured to read data from and write data to the drug delivery form information in the one or more memories.

2. The drug delivery form of claim 1, wherein the information about the drug comprises a unique identification for the form.

3. The drug delivery form of claim 2, wherein the information about the drug comprises one or more names of the drug, a dosage per form, and a type of the form, and wherein the certificate of authenticity for the manufacturer covers at least the unique identification for the form, the one or more names of the drug, the dosage per form, and the type of the form.

4. The drug delivery form of claim 1, wherein the drug comprises one or more medications.

5. The drug delivery form of claim 3, wherein the information about at least part of the supply chain comprises information concerning a pharmaceutical manufacturer of the drug delivery form, and wherein the certificate of authenticity for the manufacturer covers at least the information concerning the pharmaceutical manufacturer.

6. The drug delivery form of claim 5, wherein the information about at least part of a supply chain comprises information concerning a distributor, as one of the multiple entities, that receives the drug delivery form from the pharmaceutical manufacturer and distributes the drug delivery form to the pharmacy, and wherein the certificate of authenticity for the distributor covers at least the information concerning the distributor.

7. The drug delivery form of claim 1, wherein the drug delivery form is configured to be placed on a skin of an animal, and wherein the electronics is set to transmit based on certain conditions that indicate the drug is known to be activated.

8. The drug delivery form of claim 1, wherein the drug delivery form is configured to be ingested orally by an animal.

9. The drug delivery form of claim 1, wherein the drug delivery form is configured for one of the following: to be implanted into an animal.

10. The drug delivery form of claim 7, wherein a sensor in the electronics is triggered by sweat and the electronics is set to transmit based on the triggering of the sensor.

11. An apparatus, comprising:
one or more memories having computer readable code; and
one or more processors, wherein the one or more processors, in response to retrieval and execution of the computer readable code, cause the apparatus to perform operations comprising:
communicating with a drug delivery form comprising a drug and drug delivery form information, the drug delivery form information comprising information about the drug and about at least part of a supply chain comprising multiple entities from a manufacturer of the drug delivery form and at least to a pharmacy in the supply chain, wherein the information about at least part of the supply chain comprises information added by each of the multiple entities and information concerning the pharmacy that dispenses the drug delivery form to an animal, the information added by each of the multiple entities comprising one or more certificates of authenticity, the one or more certificates for a corresponding one of the entities used to verify the drug delivery form information is correct for that entity;
reading data from or writing data into the drug delivery form information;
accessing the one or more certificates of authenticity for a corresponding one of the entities;

verifying the corresponding added information based on the one or more certificates of authenticity; and performing the accessing and verifying for each of the entities in the supply chain that added corresponding information.

12. The apparatus of claim 11, wherein at least the reading or writing is performed using one or more encryption techniques.

13. The apparatus of claim 11, wherein the one or more processors, in response to retrieval and execution of the computer readable code, cause the apparatus to write new data corresponding to an entity at a current location in the supply chain into the drug delivery form information, including new one or more certificates of authenticity corresponding to the newly written data.

14. The apparatus of claim 11, wherein the one or more processors, in response to retrieval and execution of the computer readable code, cause the apparatus to determine a schedule at which an animal should be administered the drug based on data in the drug delivery form information and to send one or more alerts in response to the drug not being administered on the determined schedule.

15. The apparatus of claim 11, wherein the one or more processors, in response to retrieval and execution of the computer readable code, cause the apparatus to receive one or more alerts about the drug from an entity in the supply chain, and output the one or more alerts in a form to be viewed by a human being.

16. The apparatus of claim 11, wherein the drug delivery form is configured for one of the following: to be ingested orally by an animal; to be implanted into an animal; or to be placed on a skin of an animal.

17. The apparatus of claim 11, wherein the one or more processors, in response to retrieval and execution of the computer readable code, cause the apparatus to output one or more alerts in a form to be viewed by a human being, in response to verification using the one or more certificates for any one of the corresponding entities having one or more errors.

18. The apparatus of claim 15, wherein the one or more alerts indicate the drug form should not be used due to possible contamination or due to being recalled.

19. The apparatus of claim 15, wherein the apparatus is configured as a device that is wearable on a human being and wherein reading data from or writing data into the drug delivery form information further comprises sending the data read from the drug delivery form information to an other apparatus or receiving data to be written into the drug delivery form information from the other apparatus and writing the received data into the drug delivery form information.

* * * * *